US00PP28076P3

(12) United States Plant Patent
De Wit et al.

(10) Patent No.: US PP28,076 P3
(45) Date of Patent: Jun. 6, 2017

(54) APPLE TREE NAMED 'MAKALI'

(50) Latin Name: ***Malus domestica* Borkh**
Varietal Denomination: MAKALI

(71) Applicant: BETTER3FRUIT, N.V., Heverlee (BE)

(72) Inventors: Inge De Wit, Lovenjoel (BE); Hendrik Eyssen, Holsbeek (BE); Johan Keulemans, Korbeek-Lo (BE); Johan Nicolai, Sint-Truiden (BE); Els Pauwels, Amougies (BE); Paul Van Laer, Heks (BE)

(73) Assignee: Better3Fruit, N.V., Heverlee (BE)

( * ) Notice: Subject to any disclaimer, the term of this patent is extended or adjusted under 35 U.S.C. 154(b) by 0 days.

(21) Appl. No.: 14/757,272

(22) Filed: Dec. 11, 2015

(65) Prior Publication Data

US 2016/0174429 P1 Jun. 16, 2016

(30) Foreign Application Priority Data

Dec. 15, 2014 (QZ) ..... PBR 2014/3423

(51) Int. Cl.
*A01H 5/08* (2006.01)

(52) U.S. Cl.
USPC ..... Plt./161

(58) Field of Classification Search
USPC ..... Plt./161
See application file for complete search history.

*Primary Examiner* — Annette Para
(74) *Attorney, Agent, or Firm* — Foley & Lardner LLP

(57) ABSTRACT

A new and distinct variety of *Malus domestica* apple tree named 'MAKALI', particularly characterized by scab resistance (monogenic Vf), well-balanced sweet-sour taste, juicy and crisp fruit texture, good storability and shelf life.

9 Drawing Sheets

Figure 1:
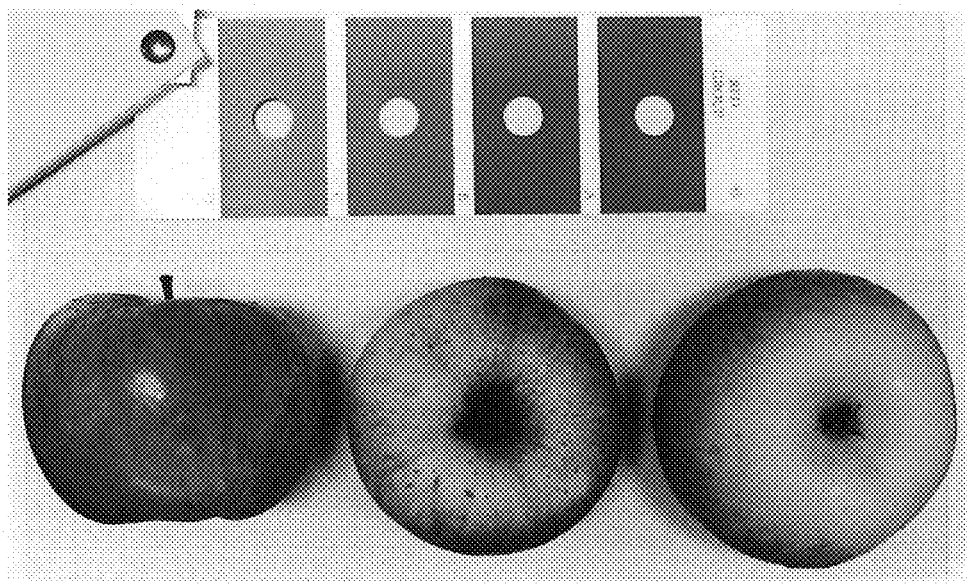

Latin name of the genus and species of the plant claimed: *Malus domestica* Borkh.

Variety denomination: 'MAKALI'.

PRIORITY CLAIM

This application claims priority under 35 U.S.C. §119(f) to European Community Plant Variety Office Application No. 2014/3423 filed Dec. 15, 2014.

BACKGROUND OF THE INVENTION

The present invention relates to a new and distinct variety of Apple tree, botanically known as *Malus domestica* Borkh of the Rosaceae family, and hereinafter referred to by the variety denomination 'MAKALI'.

The new *Malus* variety is a product of a controlled breeding program conducted by the inventors, Inge De Wit, Hendrik Eyssen, Johan Keulemans, Johan Nicolaï, Els Pauwels and Paul Van Laer in Belgium. The objective of the breeding program was to develop a new *Malus* variety with scab resistance, good taste and texture, as well as good storage capacity and shelf life.

The new *Malus* variety originated from a cross made by the inventors in 1990 in Belgium. The female or seed parent is the *Malus domestica* variety designated 'DELCORF' (registered, Plant Breeder's Rights No. FR 112364). The male or pollen parent is an unknown, proprietary variety of *Malus domestica*. The new *Malus* variety was discovered and selected by the inventors within the progeny of the stated cross in a controlled environment in 1996 in Belgium.

Asexual reproduction of the new *Malus* variety by grafting onto rootstocks was first performed in the winter of 1996-1997 in Belgium, and has demonstrated that the combination of characteristics as herein disclosed for the new variety are firmly fixed and retained through successive generations of asexual reproduction. The new variety reproduces true to type.

BRIEF DESCRIPTION OF THE INVENTION

The following traits have been repeatedly observed and are determined to be unique characteristics of 'MAKALI' which in combination distinguish this Apple tree as a new and distinct variety:

1. scab resistance (monogenic Vf);
2. well-balanced sweet-sour taste;
3. juicy and crisp fruit texture;
4. good storability; and
5. good shelf life.

In comparison to the parental variety, 'DELCORF' (registered), 'MAKALI' differs primarily in the traits listed in Table 1.

TABLE 1

| Trait | New Variety 'MAKALI' | Female Parent 'DELCORF' (registered) |
|---|---|---|
| Fruit: pattern of over color | flushed, striped and mottled | weakly defined flush with strongly defined stripes |
| Fruit: shape | obloid | globose conical |
| Fruit: time for harvest | 1 to 2 weeks after Elstar | 2 weeks before Elstar |
| Scab resistance | resistant | susceptible |

Of the many commercial varieties known to the present inventor(s), the most similar in comparison to the new *Malus* variety 'MAKALI' is the *Malus* variety 'Topaz' (registered, Plant Breeder's Rights No. CZ 322, DE APF 00111, CH 94-20-1033, EU 19951206, PLO S1, HU P9800450, SI MAD064, AR 7175, NZ APP149), in the following characteristics described in Table 2:

TABLE 2

| Characteristic | New Variety 'MAKALI' | Comparison Variety 'TOPAZ' (registered) |
|---|---|---|
| Fruit: pattern of over colour | flushed, striped and mottled | solid flush with strongly defined stripes |
| Fruit: number of lenticels | many | medium |
| Fruit: scarf skin | sometimes present | none |
| Fruit: taste | well-balanced sour-sweet | sour to very sour |

BRIEF DESCRIPTION OF THE PHOTOGRAPHS

The accompanying photographs illustrate the overall appearance of the new *Malus* variety 'MAKALI' showing the colors as true as is reasonably possible with colored reproductions of this type. Colors in the photographs may differ slightly from the color values cited in the detailed botanical description, which accurately describe the color of 'MAKALI'.

FIG. 1—shows a close-up view (side, top and bottom) of mature fruit of 'MAKALI'.

Figure 2:
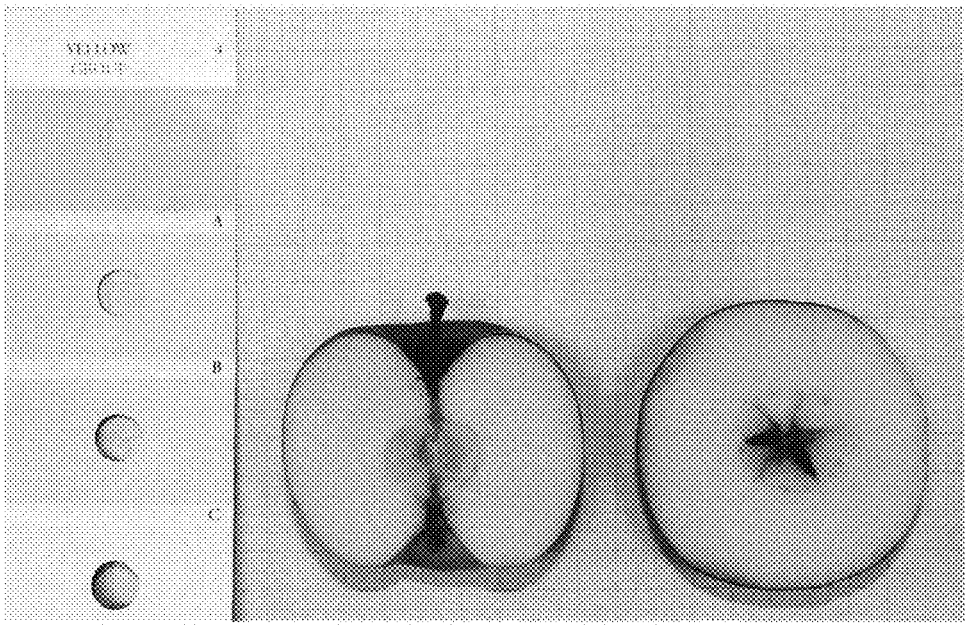

FIG. 2—shows dissection views of mature fruit of 'MAKALI'.

Figure 3:
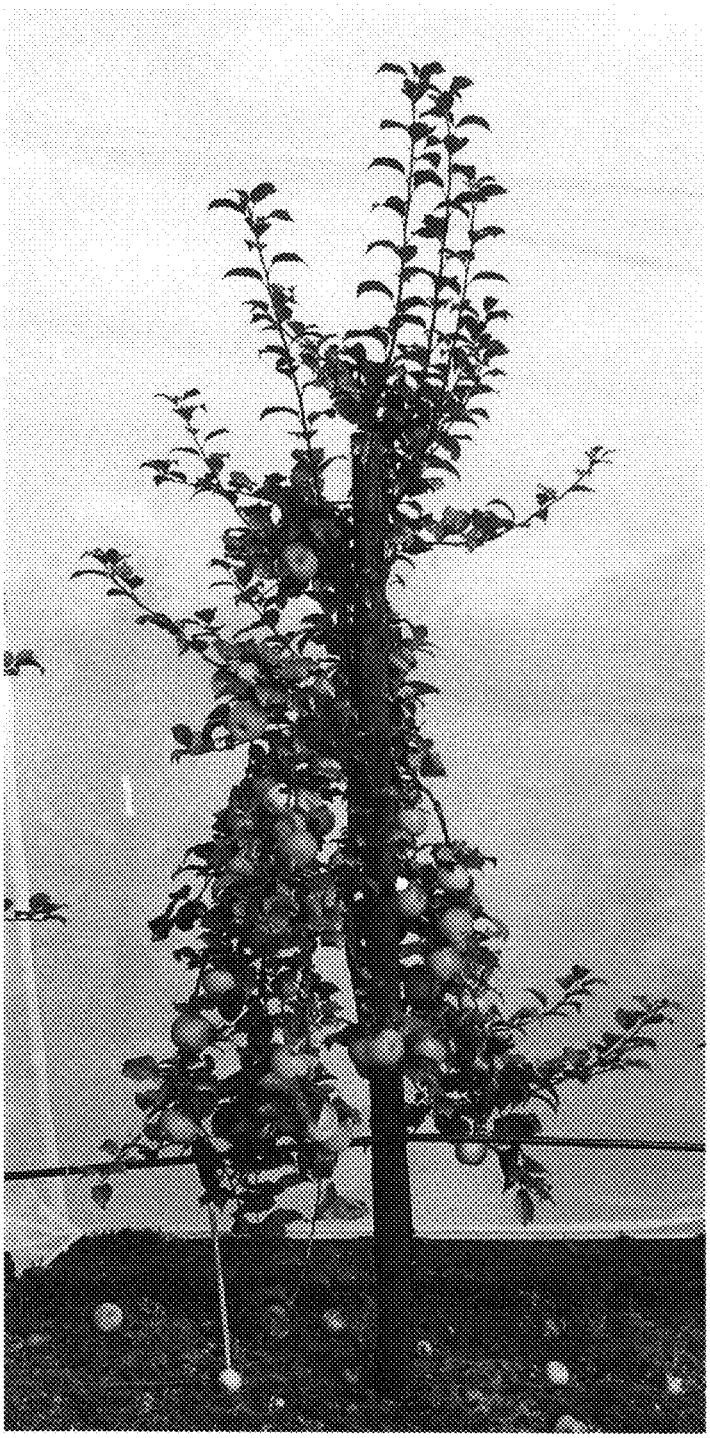

FIG. 3—shows a fruit-bearing tree of 'MAKALI', at 8 years of age.

Figure 4:
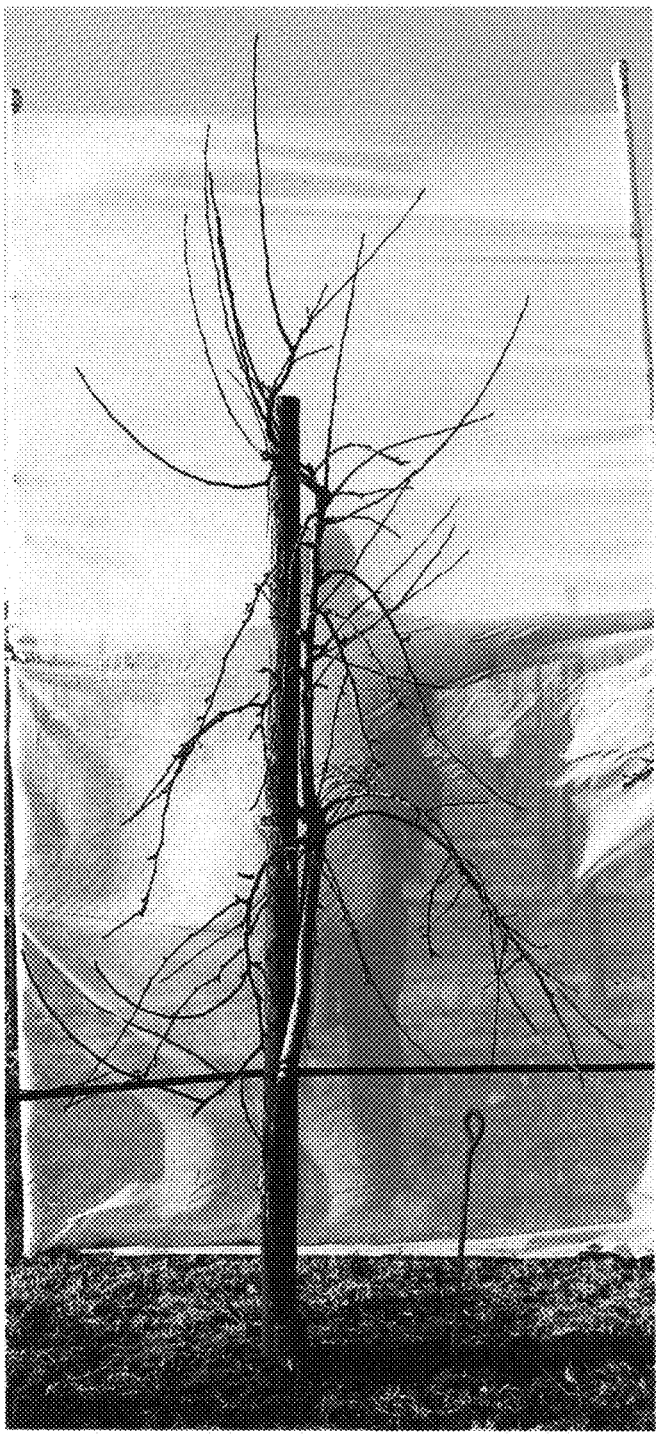

FIG. 4—shows a dormant tree of 'MAKALI', at 8 years of age

Figure 5:
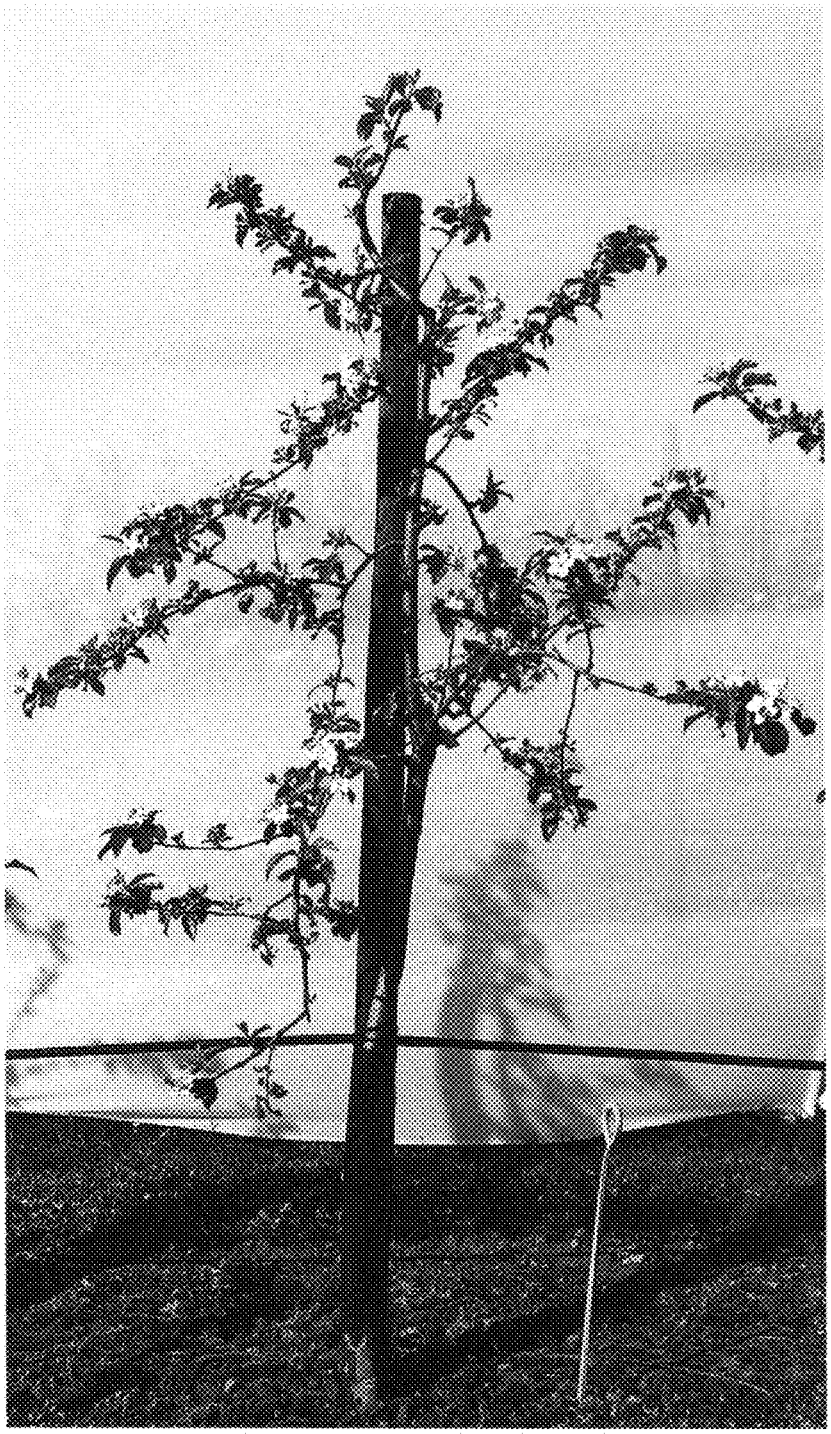

FIG. 5—shows a blooming tree of 'MAKALI', at 8 years of age.

Figure 6:
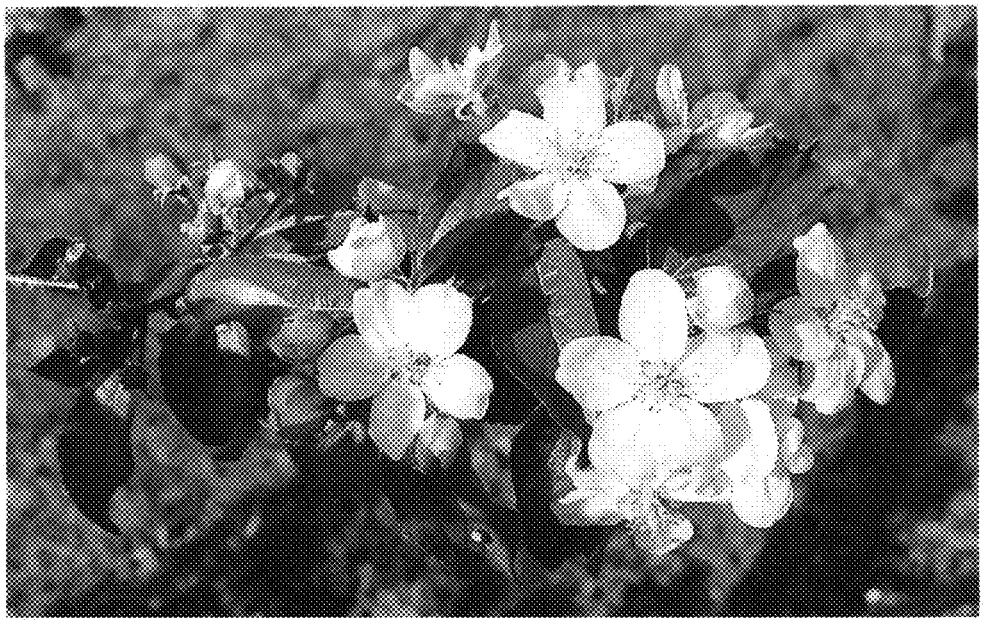

FIG. 6—shows inflorescence of 'MAKALI'.

Figure 7:
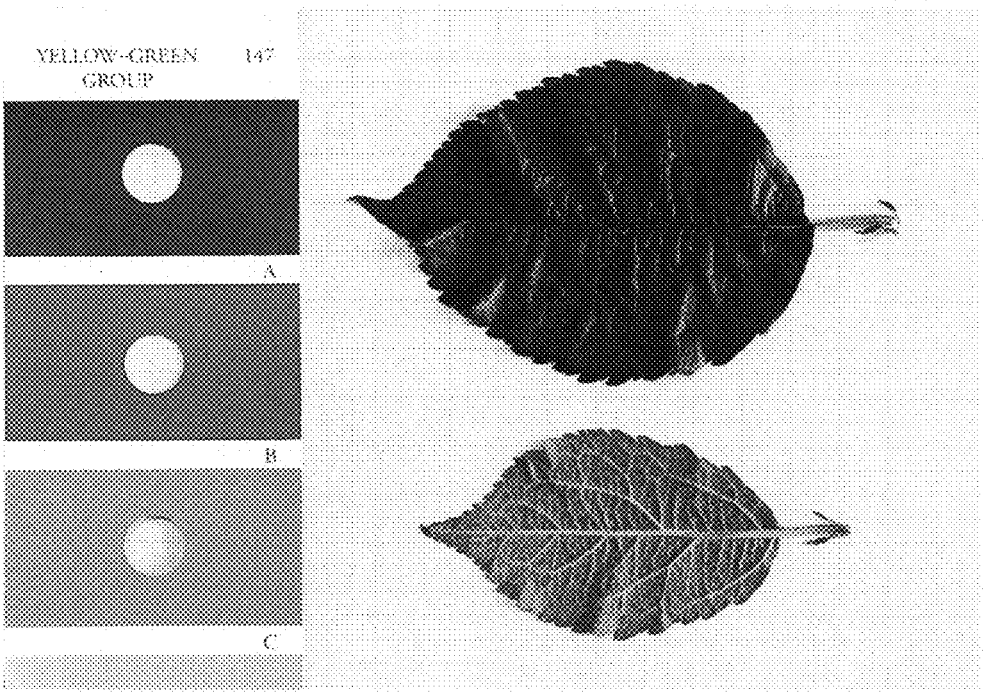

FIG. 7—shows the upper surface (top) and under surface (bottom) view of leaves of 'MAKALI'.

Figure 8:
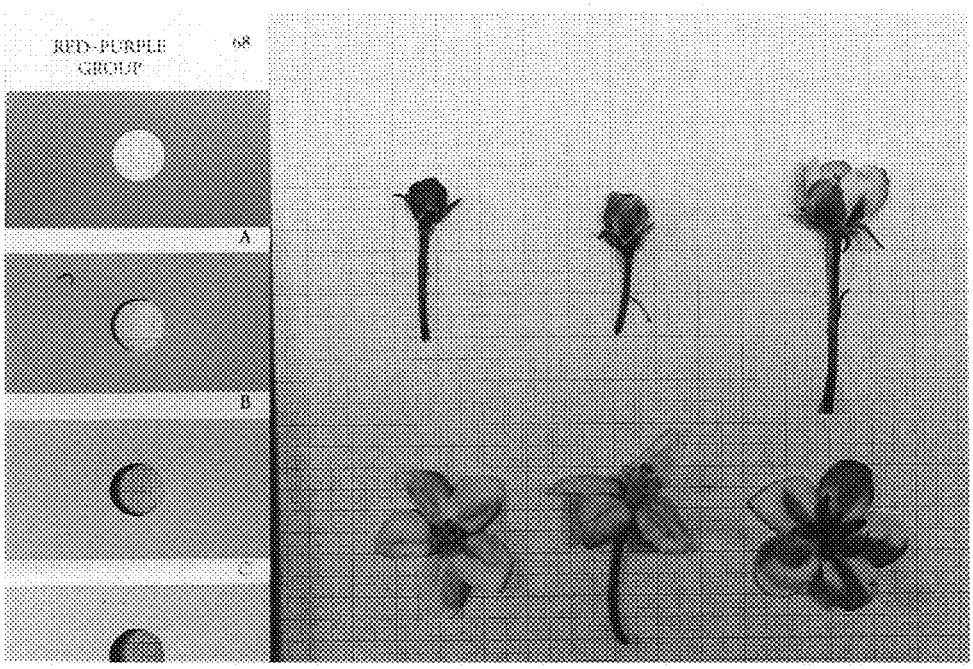

FIG. 8—shows different stages of development of the flowers and the (from left to right) top, side and bottom view of a fully expanded flower of 'MAKALI'.

Figure 9:
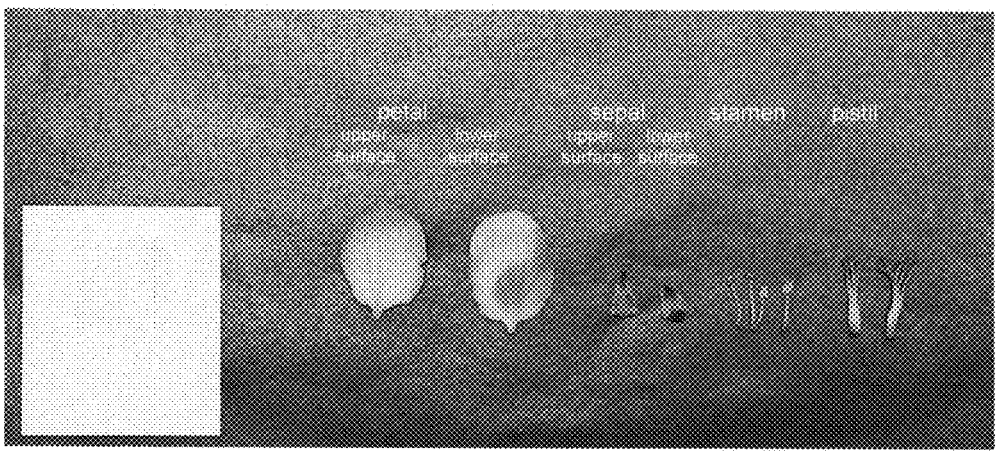

FIG. 9—shows different parts of a flower of 'MAKALI' (from left to right: upper and lower surface of petal, upper and lower surface of sepal, stamen, pistil).

DETAILED BOTANICAL DESCRIPTION

The new *Malus* variety 'MAKALI' has not been observed under all possible environmental conditions. The phenotype of the new variety may vary with variations in environment such as temperature, light intensity, and day length without any change in the genotype of the Apple tree.

The aforementioned photographs, together with the following observations, measurements and values describe trees of 'MAKALI' as grown in Rillaar, Belgium, under conditions which closely approximate those generally used in commercial practice.

Unless otherwise stated, the detailed botanical description includes observations, measurements and values based on 8 years old 'MAKALI' trees grown in Rillaar, Belgium from 2009 to 2015. Quantified measurements are expressed as an average of measurements taken from a number of trees of 'MAKALI'. The measurements of any individual tree, or any group of trees, of the new variety may vary from the stated average.

Color references are made to The Royal Horticultural Society Colour Chart (R.H.S.), (4$^{th}$ edition, 2001), except where general colors of ordinary significance are used. Color values were taken under daylight conditions.

All of the trees of 'MAKALI', insofar as they have been observed, have been identical in all the characteristics described below.

Classification:

*Botanical.*—*Malus domestica.*

Parentage:

*Female or seed parent.*—*Malus* variety designated 'DELCORF' (registered).

*Male or pollen parent.*—Unknown, proprietary variety of *Malus domestica.*

Propagation: Grafting onto rootstocks.

Growing conditions:

*Light intensities.*—Full sunlight.

*Temperature.*—During day, grown in range of 2° C. to 23° C., and during evening, grow in range of −5° C. to 13° C. (based on average month temperature).

Tree:

*Age.*—Observed trees were 8 years old.

*Vigor.*—Medium.

*Form.*—Ramified, drooping.

*Habit.*—A medium-sized tree with one trunk and 5+/−2 leaders; main branches drooping; crown symmetrical.

*Branching habit.*—Main branches angle is 84+/−10° with respect to trunk if allowed to grow naturally.

*Density.*—About 2200 trees per hectare.

*Cropping behavior.*—Normal beginning production; low to medium productivity; low to regular flowering; biennial bearing.

*Type of bearing.*—On spurs and long shoots.

*Production.*—About 14.9 kg per tree in 2013.

*Size at maturity.*—Height: About 215+/−7 cm. Spread: About 121+/−11 cm.

*Trunk.*—Height (up to leaders): About 100+/−10 cm. Diameter: About 3.3+/−0.2 cm. Texture: Slightly rough. Bark color: Primarily RHS 164A, with underbark RHS 156A. Trunk Lenticels: Length: About 3.2+/−0.6 mm. Width: About 1.2+/−0.3 mm. Color: RHS 161B. Density: About 3.6 +/−1.4 n° per cm$^2$.

*Branches.*—Number per tree: About 33+/−8. Length: maximum 67+/−20 cm; minimum 5+/−3 cm. Diameter (at 2 years): About 11+/−3 mm. Surface texture: slightly rough. Pubescence: none. Color: Mature (after about 3 years old): RHS 166B. New Growth: RHS 200B. Internode length: About 31+/−10 mm. Internode diameter: About 6+/−1 mm. Branch lenticels: Length: About 2.9+/−0.9 mm. Width: About 1.2+/−0.4 mm. Color: RHS 161C. Density: About 4.2+/−1.9 n° per cm$^2$.

*Spur.*—Present: Yes. Distance between each spur: On the 2 and 3 year old branches, the distance is about 4+/−2 cm. Diameter of each spur: About 5+/−1 mm. Number of fruit per spur: About 0.8+/−0.8.

Foliage:

*Arrangement.*—Alternate, simple, petiolated.

*Lamina.*—Size: Length: About 84+/−13 mm (fully expanded leaf). Width: About 53+/−12 mm (fully expanded leaf). Length/width ratio: 1.6+/−0.1.

*Overall shape.*—Obtuse but with a small pointy tip, petiolated. Base shape: rounded. Apex shape: acuminate.

*Margin*.—Serrate. Texture: Upper surface: smooth, glabrous. Under surface: smooth, medium pubescence (white). Attitude in relation to shoot: outwards. Color (mature leaves): Upper surface: RHS 147A. Under surface: RHS 138B. Color (immature leaves): Upper surface: RHS 143A. Under surface: RHS 138B.

*Venation*.—Type: Pinnate. Color: RHS 144D.

*Petiole*.—Length: About 17+/−4 mm. Diameter: About 1.8+/−0.3 mm. Texture: smooth, high pubescence (white). Color: RHS 143C (upper surface), RHS 144D (lower surface), RHS 59B (at the petiole base, upper and lower surface).

*Stipule*.—Arrangement: free standing. Length (distance of stipules from basal attachment of petiole): About 8.3+/−1.7 mm. Width: About 1.6+/−0.5 mm.

Inflorescence:

*Blooming time*.—Very early to early (after Ein Shemer, before Idared and Boskoop).

*Blooming period*.—About 1 week.

*Fragrance*.—Quite strong.

*Type*.—Corymb.

*Number of flowers per inflorescence*.—About 5.1+/−0.8.

*Inflorescence size*.—Diameter: About 80+/−10 mm. Depth: About 47+/−7 mm.

*Buds*.—Terminal Buds: Number per spur: About 1. Shape: a cone with an ellipsoidal base. Length: About 6.8+/−1.6 mm. Width: About 4.2+/−0.4 mm. Texture: smooth, high pubescence. Color: Apex RHS 200A, base RHS N186C. Scales: Number: About 5.0+/−1.1. Overall shape: triangular, folded double around bud. Apex shape: acuminate or 3 sharp points. Base shape: straight, fully grown together at base Color: Upper: RHS 187A. Lower: RHS 144D. Lateral Buds: Number per spur: About 3.1+/−2.4. Shape: a cone with an ellipsoidal base. Length: About 3.5+/−0.9 mm. Width: About 2.9+/−0.5 mm. Texture: smooth, slight pubescence at apex. Color: RHS 187B (apex and base). Scales: Number: About 4.7+/−1.1. Overall shape: triangular, folded double around bud. Apex shape: acute. Base shape: straight, fully grown together at base. Color: Upper: RHS N186C. Lower: RHS 144B.

*Petals*.—Arrangement: overlapping. Number per flower: 5. Size: Length: About 16+/−2 mm. Width: About 13+/−1 mm. Length/width ratio: 1.3+/−0.2. Overall shape: ovate. Apex shape: rounded. Base shape: rounded. Texture (upper surface): smooth, with hairs. Texture (lower surface): smooth, no hairs. Margin: entire. Color (upper surface): Apex RHS N66D; base RHS N155B. Color (lower surface): Apex RHS 68A; base RHS 69D.

*Sepals*.—Number per flower: 5. Size: Length: About 8.6+/−1.4 mm. Width: About 4.2+/−0.5 mm. Length/width ratio: 2.1+/−0.4. Overall shape: triangular. Apex shape: aristate. Base shape: truncate. Texture (upper surface): smooth, hairy. Texture (lower surface): smooth, slightly hairy. Margin: entire. Color (upper surface): Apex RHS 166A, base RHS 143C. Color (lower surface): Apex RHS 166A, base RHS 143C.

*Pedicel*.—Length: 32+/−5 mm. Diameter: 1.6+/−0.2 mm. Texture: smooth, hairy (white hairs). Color: RHS 144B.

Fruit:

*Keeping quality*.—The fruit can be stored in cold temperature conditions for up to 2 months (normal atmosphere). It has a shelf life of about 2 weeks.

*Maturity when described*.—Ripe for eating, 2 weeks storage.

*Maturity period after full bloom*.—About 5 months after full bloom.

*Date of first and last picking* (*harvest*).—About $2^{nd}$ and $3^{th}$ week of September.

*Type*.—Pome.

*General shape*.—Obloid.

*Average weight*.—About 171+/−30 g.

*Fruit size*.—Average height: About 61+/−5 mm. Average diameter (at widest point): About 77+/−4 mm. Position of maximum diameter: middle. Height/thickness ratio: 0.80+/−0.04.

*Stem*.—Length: About 23+/−7 mm. Diameter: About 2.1+/−0.2 mm. Color: RHS 164A (full length, one side), RHS 144B (full length, one side), RHS 175B (at the end).

*Stalk cavity*.—Depth: About 16.3+/−1.9 mm. Width: About 38.2+/−8.3 mm.

*Eye basin*.—Depth: About 9.9+/−1.8 mm. Width: About 36.9+/−2.7 mm. Crowning at calyx end: moderate. Position of sepals: closed. Calyx tube: partly open.

*Skin*.—Thickness: 0.3+/−0.1 mm. Texture: tough. Bloom: absent. Greasiness: absent. Firmness (at picking time): 6.1+/−0.8 kg/cm$^2$. Overcolor color: RHS 45C and RHS 50B. Percentage of skin surface with overcolor color: About 50%. Pattern of overcolor: flushed, striped and mottled. Intensity of overcolor: medium. Ground color: RHS 150D and RHS 154D. Skin Lenticels: Length: About 1.7+/−0.4 mm. Width: About 1.4+/−0.3 mm. Color: RHS 152C. Density: About 3.3+/−2.2 n° per cm$^2$.

*Flesh*.—Color: RHS 4D. Texture: crisp and juicy. Aroma: moderate. Eating quality: well-balanced sour-sweet. Sugar content (at picking time): 13.3+/−0.6 Brix. Acidity/Starch (at picking time) 6.3+/−0.2 g/l malic acid. Core: Symmetry of core: round. Distinctness of core lines: medium. Locules: Number (per fruit): 5. Length: About 8+/−1 mm. Width: About 3+/−1 mm. Form: teardrop shape.

Seeds:

*Number per fruit*.—About 6.5+/−1.7.

*Number per locule*.—About 1.1+/−0.7.

*Shape*.—Teardrop shape.

*Length*.—About 9.4+/−0.6 mm.

*Width*.—About 4.5+/−0.4 mm.

*Texture*.—Smooth.

*Color*.—RHS 175A.

Reproductive organs:

*Androecium*.—Stamen: Number per flower: 18.6+/−1.2. Length: About 7.2+/−1.1 mm. Anther: Length: About 2.2+/−0.3 mm. Color: RHS 11B. Filaments: Length: About 5.8+/−1.2 mm. Color: RHS 155B. Pollen: Amount: moderate. Color: RHS 4A. Pollination Requirements: cross pollination.

*Gynoecium*.—Pistils: Quantity: 5. Length: About 11.9+/−1.3 mm. Stigmas: Length: About 1.3+/−0.4 mm. Color: RHS 144B. Ovary: Length: About 4.9+/−0.8 mm. Width: About 1.8+/−0.4 mm. Color: RHS 144C.

Use: Fresh market.

Disease/pest resistance: Resistant to scab (*Venturia inaequalis*, monogenic Vf).

Disease/pest susceptibility: Tolerant to powdery mildew (*Podosphaera inaequalis*) and canker (*Nectria galligena*); medium susceptible to wooly apple aphid (*Eriosoma lanigerum*); susceptible to fire blight (*Erwinia amylovora*).

Winter hardiness: Tolerant to temperatures down to −10° C. without observed damage to wood and buds of dormant apple trees.

Drought/heat tolerance: Tolerant to temperatures up to 40° C., growth is limited by drought periods without irrigation.

Shipping/storage characteristics: Not sensitive to bruising; good storability under ULO-conditions (maintains high quality for up to 5 months).

We claim:

1. A new and distinct variety of *Malus domestica* apple tree named 'MAKALI', as illustrated and described herein.

* * * * *